United States Patent
Teichman et al.

(10) Patent No.: US 9,265,497 B2
(45) Date of Patent: Feb. 23, 2016

(54) TISSUE ACCESS SITE SYSTEM AND METHOD

(75) Inventors: Eyal Teichman, Hod-HaSharn (IL); Tanhum Feld, Moshav Merhavia-Doar-Na Izrael (IL); Michal Geva, Ramat-HaSharon (IL); Guy Kotlizky, Kfar-Shemaryahu (IL)

(73) Assignee: APICA CARDIOVASCULAR IRELAND LIMITED, Galway (IE)

( * ) Notice: Subject to any disclaimer, the term of this patent is extended or adjusted under 35 U.S.C. 154(b) by 747 days.

(21) Appl. No.: 13/002,767

(22) PCT Filed: Jul. 6, 2009

(86) PCT No.: PCT/IL2009/000673
§ 371 (c)(1),
(2), (4) Date: Jan. 6, 2011

(87) PCT Pub. No.: WO2010/004552
PCT Pub. Date: Jan. 14, 2010

(65) Prior Publication Data
US 2011/0118759 A1    May 19, 2011

Related U.S. Application Data

(60) Provisional application No. 61/129,589, filed on Jul. 7, 2008, provisional application No. 61/129,583, filed on Jul. 7, 2008.

(51) Int. Cl.
*A61B 17/04* (2006.01)
*A61B 17/00* (2006.01)
(Continued)

(52) U.S. Cl.
CPC ......... *A61B 17/0482* (2013.01); *A61B 17/0057* (2013.01); *A61B 17/3415* (2013.01);
(Continued)

(58) Field of Classification Search
CPC ........... A61B 17/0057; A61B 17/0482; A61B 17/3415; A61B 17/3417; A61B 17/32053; A61B 17/3209; A61B 2017/00637; A61B 2017/00663; A61B 2017/00672; A61B 2017/00778; A61B 2017/0472; A61B 2017/22038; A61B 2017/3454; A61B 17/3421; A61B 17/3423; A61B 2017/3425; A61B 2017/3427; A61B 2017/3429
USPC .................................. 606/144, 151, 191, 213
See application file for complete search history.

(56) References Cited

U.S. PATENT DOCUMENTS 5,372,588 A * 12/1994 Farley ................ A61B 17/3417
604/170.01
5,417,699 A * 5/1995 Klein .................. A61B 17/0057
112/169

(Continued)

FOREIGN PATENT DOCUMENTS

EP          2 303 389         4/2011
JP          2006-514561 A     5/2006
(Continued)

OTHER PUBLICATIONS

Office Action Dated Jan. 23, 2012 From the Israel Patent Office Re. Application No. 210531 and Its Translation Into English.
(Continued)

*Primary Examiner* — Julian W Woo
*Assistant Examiner* — Shaun L David
(74) *Attorney, Agent, or Firm* — Kilpatrick Townsend & Stockton LLP

(57) ABSTRACT

A tissue access site system is provided. In one embodiments, the system includes a tissue cutting element designed for generating a tissue access site through a tissue, the tissue access site being surrounded by tissue edge portions of a predetermined geometry; and a tissue closure device being for attaching at least one closure element to the tissue at a region corresponding to at least one of the tissue edge portions.

25 Claims, 15 Drawing Sheets

(51) Int. Cl.
*A61M 29/00* (2006.01)
*A61B 17/34* (2006.01)
*A61B 17/3205* (2006.01)
*A61B 17/3209* (2006.01)
*A61B 17/22* (2006.01)

(52) U.S. Cl.
CPC ......... *A61B17/3417* (2013.01); *A61B 17/3209* (2013.01); *A61B 17/32053* (2013.01); *A61B 2017/00637* (2013.01); *A61B 2017/00663* (2013.01); *A61B 2017/00672* (2013.01); *A61B 2017/00778* (2013.01); *A61B 2017/0472* (2013.01); *A61B 2017/22038* (2013.01); *A61B 2017/3454* (2013.01); *A61M 29/00* (2013.01)

(56) References Cited

U.S. PATENT DOCUMENTS

| | | | |
|---|---|---|---|
| 5,830,125 | A | 11/1998 | Scribner et al. |
| 5,846,253 | A * | 12/1998 | Buelna .................. A61B 17/04 606/144 |
| 6,280,460 | B1 * | 8/2001 | Bolduc .............. A61B 17/0469 606/144 |
| 2002/0049453 | A1 * | 4/2002 | Nobles ............... A61B 17/0057 606/139 |
| 2003/0167083 | A1 | 9/2003 | Lashinski et al. |
| 2003/0216756 | A1 | 11/2003 | Klein et al. |
| 2004/0092985 | A1 * | 5/2004 | Parihar et al. ................. 606/167 |
| 2005/0070924 | A1 * | 3/2005 | Schaller et al. ............... 606/142 |
| 2005/0267520 | A1 | 12/2005 | Modesitt |
| 2006/0095056 | A1 | 5/2006 | Douglas et al. |
| 2006/0287673 | A1 | 12/2006 | Brett et al. |
| 2007/0073389 | A1 | 3/2007 | Bolduc et al. |
| 2007/0255296 | A1 | 11/2007 | Sauer |
| 2008/0086075 | A1 | 4/2008 | Isik et al. |
| 2008/0097479 | A1 | 4/2008 | Boehlke et al. |
| 2008/0210737 | A1 * | 9/2008 | Ginn .................... A61B 17/083 227/175.1 |
| 2010/0145364 | A1 * | 6/2010 | Keren ................ A61B 17/0469 606/144 |

FOREIGN PATENT DOCUMENTS

| | | |
|---|---|---|
| JP | 2011-527226 A | 10/2011 |
| WO | WO94/13211 A1 | 6/1994 |
| WO | 95/13021 A1 | 5/1995 |
| WO | 2004/030513 A2 | 4/2004 |
| WO | WO 2010/004552 | 1/2010 |

OTHER PUBLICATIONS

International Search Report and the Written Opinion Dated Nov. 10, 2009 From the International Searching Authority Re.: Application No. PCT/IL09/00673.

International Preliminary Report on Patentability Dated Jan. 20, 2011 From the International Bureau of WIPO Re. Application No. PCT/IL2009/000673.

Supplementary European Search Report for EP Application No. 09794096 mailed Nov. 19, 2013.

Israeli Office Action for Israeli Application No. 210531 dated Jun. 30, 2013, received Jul. 11, 2013 (8 pages including English translation).

Japanese Office Action for Japanese Application No. 2011-517309 mailed Sep. 10, 2013 (4 pages, English translation).

Japanese Office Action mailed Jun. 13, 2014 for JP Application No. 2011-517309 (2 pages).

Patent Examination Report No. 1 for corresponding Australian Patent Application No. 2009269566 dated Apr. 7, 2014, 4 pages.

* cited by examiner

DETAIL E
SCALE 10:1

TISSUE ACCESS SITE SYSTEM AND METHOD

RELATED APPLICATIONS

This Application is a National Phase of PCT Patent Application No. PCT/IL2009/000673 having International filing date of Jul. 6, 2009, which claims the benefit of U.S. Provisional Patent Application Nos. 61/129,589 and 61/129,583 both filed on Jul. 7, 2008. The contents of the above Applications are all incorporated herein by reference.

FIELD AND BACKGROUND OF THE INVENTION

The present invention relates to a system and method for opening/dilating and closing a tissue access site and, more particularly, to a system which can be used to open/dilate and close large vascular access sites, such as those utilized in femoral vascular access.

More than five million percutaneous interventions are performed annually in the United States, involving femoral artery catheterization for diagnostic or therapeutic purposes.

Most procedures are performed through small sheath access sites (5-8F) and thus closure of such access sites can be effected using manual or mechanical compression for 15-30 minutes, typically combined with an extended bed-rest of three to six hours.

However, manual compression can cause patient discomfort, and is time- and resource-intensive, and as such, a need for quicker, more patient compatible closure has led to the introduction of closure devices in the early 1990s. Since then, vascular closure systems have been simplified to provide wider patient access to a range of vascular procedures. Now available from many sources, these devices shorten procedure times, allow patients to ambulate earlier, minimize bleeding and possibly reduce costs associated with hospital care.

At present there are dozens of devices on the market or at various stages of development, such devices employ sutures, patches, glue, coagulants and/or staples or a source of energy to effectively seal access sites post procedure.

Although these devices were specifically designed for closure of small access sites (<10F), there have been attempts since the late 90s to utilize suture closure devices (specifically the Sutura and Perclose devices) in large bore access sites >18F, illustrating at least a limited need for 'automated' closure of large access sites. Large bore access site closure is typically effected via manual suturing of an exposed artery and thus requires presence of a specialist while being time consuming as well as more invasive.

The studies performed to date illustrate that closure of access sites less than 18F in size via such devices is effective and highly successful, whereas closure of larger bore access sites (e.g. 22F) is less effective.

Although at present the number of procedures effected through large bore access sites is small, current trends anticipate that the number of such procedures will rise in the future and although a concomitant reduction in sheath sizes might also take place, such reduction will still place average sheath size at over 18F.

While reducing the present invention to practice, the present inventors have devised an access site system which provides the physician with control over access site generation and closure.

SUMMARY OF THE INVENTION

According to one aspect of the present invention there is provided a tissue access site system comprising: (a) an element designed for generating a tissue access site through a tissue, the tissue access site being surrounded by tissue edge portions of a predetermined geometry; and (b) a tissue closure device being for attaching at least one closure element to the tissue at a region corresponding to at least one of the tissue edge portions.

According to another aspect of the present invention there is provided a method of providing access through tissue comprising: (a) cutting through a tissue to generate a tissue access site surrounded by tissue edge portions of a predetermined geometry; (b) attaching at least one closure element to the tissue at a region corresponding to at least one of the tissue edge portions; and (c) using the tissue access site to gain access through the tissue.

According to further features in preferred embodiments of the invention, step (b) is effected prior to step (a).

According to still further features in the described preferred embodiments the tissue cutting element is designed for cutting a cross pattern through the tissue.

According to still further features in the described preferred embodiments the tissue cutting element is designed for generating a tissue edge portion having a triangular geometry.

According to still further features in the described preferred embodiments the tissue cutting element is designed for cutting the tissue access site going into the tissue.

According to still further features in the described preferred embodiments the tissue cutting element is designed for going into the tissue through and cutting the tissue access site coming out of the tissue.

According to still further features in the described preferred embodiments the at least one closure element is a suture and further wherein the tissue closure device includes at least one tissue piercing element.

According to still further features in the described preferred embodiments the system is configured for coordinating operation of the tissue cutting element and the tissue closure device, such that at least one closure element is attached to the tissue at a region corresponding to at least one of the tissue edge portions prior to, during or following generation of the tissue access site.

According to still further features in the described preferred embodiments the tissue closure device is a suturing device capable of threading a suture in and out of the tissue.

According to still further features in the described preferred embodiments the at least one closure element is a clip.

According to still further features in the described preferred embodiments the tissue cutting element and the tissue closure device are integrated into a single housing.

According to still further features in the described preferred embodiments the system further comprises a patch delivery device for delivering a patch to the tissue.

According to still further features in the described preferred embodiments the system further comprises an adhesive or sealant delivery device.

According to yet another aspect of the present invention there is provided a method of performing a procedure requiring access through tissue comprising: (a) cutting through a tissue to generate a tissue access site surrounded by tissue edge portions of a predetermined geometry; (b) attaching at least one closure element to the tissue at a region corresponding to at least one of the tissue edge portions; (c) performing the procedure through the tissue access site; and (d) closing the tissue access site using the at least one closure element.

According to still further features in the described preferred embodiments step (b) is effected prior to step (a).

According to still another aspect of the present invention there is provided a tissue access site system comprising: (a) a tissue dilating element designed for dilating a hole in a tissue; and (b) a tissue closure device being for attaching at least one closure element to the tissue around the hole.

According to still further features in the described preferred embodiments the tissue dilating element is designed for positioning over a guide-wire.

According to still further features in the described preferred embodiments the tissue dilating element is designed for controllably dilating the hole so as to minimize tissue damage around the hole.

According to still further features in the described preferred embodiments the at least one closure element is a suture and further wherein the tissue closure device includes at least one tissue piercing element.

According to still further features in the described preferred embodiments the system is configured for coordinating operation of the tissue dilating element and the tissue closure device, such that at least one closure element is attached to the tissue around the hole prior to, during or following dilation thereof.

According to still further features in the described preferred embodiments the tissue closure device is a suturing device capable of threading a suture in and out of the tissue.

According to still further features in the described preferred embodiments the at least one closure element is a clip.

According to still further features in the described preferred embodiments the tissue dilating element and the tissue closure device are integrated into a single housing.

According to still another aspect of the present invention there is provided a device for generating an access site in a tissue comprising a blade having a cutting pattern capable of forming an access site having one or more flaps of tissue.

According to still another aspect of the present invention there is provided a balloon catheter configured for accessing an ipsi-lateral blood vessel from a contra-lateral entry site.

According to still further features in the described preferred embodiments, the balloon catheter includes a compliant balloon.

The present invention successfully addresses the shortcomings of the presently known configurations by providing a system which can be used to control access site generation and closure.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
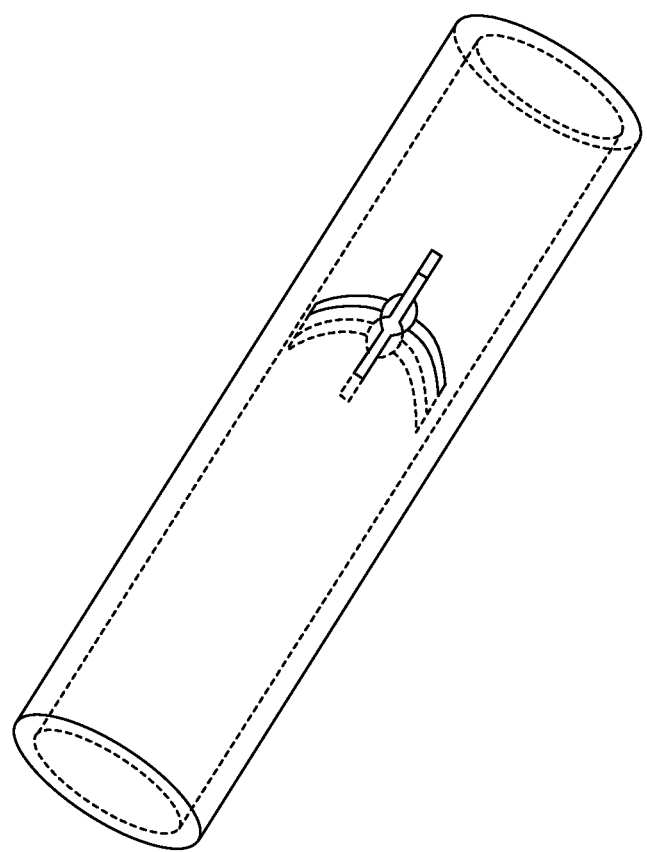
FIGS. 1A-B illustrate two tissue cutting patterns demonstrating the resulting edge portion geometry formed by the tissue cuts.

The present invention is of a system for complete or partial closure of a tissue access site and optionally of creating the access site and preparing it for subsequent closure. Specifically, the present invention can be used to close or reduce an access site to a lumen of a hollow tissue structure such as a vessel while also optionally enabling controlled generation of the access site and preparation thereof for closure or reduction.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Access to body cavities and lumens of organs and vessels can be achieved through tissue access sites. For example, in the case of percutaneous vascular procedures, a tissue access site created through a wall of an artery enables a physician to guide and deploy various instruments through the lumen of the artery.

The size of the access site depends on the type of procedure and instrument used. Though most types of procedures utilize relatively small access sites (<8F) which can be later closed via manual compression, such compression can cause patient discomfort, and is time- and resource-intensive, and as such, a need for quicker, more patient compatible closure has led to the introduction of closure devices.

Such devices were specifically designed for closure of small access sites, however, introduction of procedures that require larger access sites, such as percutaneous valve replacement, trans- or intra-aortic pump placement and AAA repair has initiated attempts to utilize closure devices in large bore access sites (>12F) illustrating a need for 'automated' closure of large access sites.

While reducing the present invention to practice, the present inventors have identified a need for a closure system that would enable efficient closure of large bore access sites as well as small bore access sites.

The present inventors postulated that in order for such a system to be effective in closing large bore access sites, control over access site geometry and placement of closure elements is crucial.

Vascular access sites are presently generated by inserting a dilating sheath into a needle puncture hole in the blood vessel. The dilating sheath dilates the blood vessel tissue to a desired size at which point the dilating sheath is either replaced or used as the working sheath. Dilation of the access site and subsequent manipulation of the working sheath can result in vascular tissue tearing and damage around the access site thus severely impacting subsequent closure.

As is further described hereinunder, the present system incorporates a tissue cutting/nicking element for generating a tissue access site of a prescribed shape (e.g. geometry of formed edge portions) and size and a tissue closure device which is capable of attaching tissue closure elements (e.g. sutures) at specific tissue regions around the access site, thereby optimizing tissue attachment of the closure elements. The present inventors believe that the unique combination of controlled tissue cutting and precise closure element attachment provides a tissue access site which is capable of maintaining access site integrity throughout a procedure while at the same time facilitates subsequent closure while ensuring maximal closure efficacy.

Thus, according to one aspect of the present invention there is provided a system for creating a tissue access site and for preparing the access site for subsequent closure (also referred to herein as "tissue access site system" or the "present system").

The present system includes two independently actuatable components which can be integrated into a single housing or be separately housed.

The first component includes a tissue cutting/nicking element which is designed for facilitating the generation of a tissue access site through a tissue. The tissue can be any tissue which defines a wall of a cavity within the body or a lumen of a vessel. Examples of tissue include vascular tissue, abdominal tissue and the like.

The tissue cutting/nicking element is configured such that the access site formed thereby is surrounded (defined) by tissue edge portions having a predetermined geometry.

Regardless of the cut pattern or extent of cutting (e.g. nicking or complete cut), tissue cutting is effected in a way which enable subsequent introduction of a medical instrument through the access site formed by the cut. For example, the tissue can be completely cut to form an access site which enables direct introduction of the medical instrument, or it can be partially cut and then controllably dilated (via, for example a dilator) to generate the access site. In cases where the tissue is partially cut (e.g. nicked or scored), forcible dilation of the nicked or scored tissue can lead to controllable tissue reaping and generation of an access site of a desired size.

In any case, when used to generate a vascular access site, the present invention facilitates introduction of a medical instrument through a working sheath which is first introduced into the access site and provides a conduit for the medical instrument (e.g. catheter). To accommodate the medical instrument or sheath (which can have a bore size as large as 24F or more) the tissue cut is selected such that the edge portions generated by the cut or nick in the tissue can be folded into the lumen of the tissue when a medical device is pushed through the access site, essentially acting as push-in flaps. Such folding provides the largest possible access site while minimizing tissue stress which can lead to tissue tearing and alteration to access site shape and size.

Figure 1B:
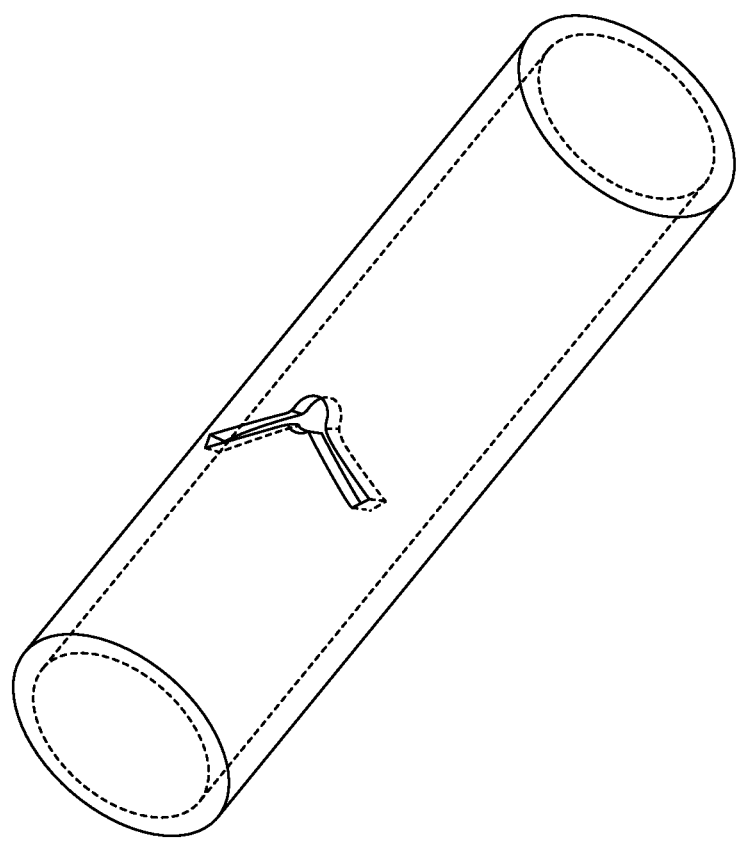

FIGS. 1a-b illustrate various tissue cutting patterns which result in predefined edge portion geometry and predefined access site shape and size. FIG. 1a illustrates a cross-shaped cutting pattern which results in four triangular tissue edge portions each having a 90 degree angle, while FIG. 1b illustrates a V-shaped cutting pattern which results in a v-shaped flap. Other cutting patterns can include a Y, U or straight radial or axial cutting patterns. In any case, the cut is effected such that the dimension of the formed access site are smaller than the working sheath inserted therethrough, thus minimizing any blood leakage during a procedure. For example, an X or V-shaped cut pattern can be effected such that the resulting access site is about 12-18F in size and is dilated to fit a 22F sheath.

The tissue cutting element includes a tissue cutting head which is configured for cutting the pattern through the tissue. The cutting head can be configured to cut the tissue from the outside of the tissue and into the lumen, or in the reverse direction when exiting the lumen of the tissue. In the latter case, a cutting head having deployable cutting blades can be introduced into the lumen of the tissue through a small puncture (e.g. 3F) and the blades deployed within the lumen. The cutting head can then be pulled out of the tissue to generate the cut pattern. A stopper element can be incorporated into the cutting blade or the cutting head to serve as a stop against the tissue thus preventing any damage to peripheral tissues. For example, in the case of an artery, such a stopper element can be positionable above the blades such that when the blades cut through the artery wall, the stopper element would stop further cutting into the tissue when the blades reach a predetermined depth.

The cutting head can include blades (e.g. fabricated from stainless steel, Nitinol, ceramic and the like) wires (e.g. cauterization wires), water jets, a sonic scalpel or any device capable of cutting tissue. Cutting blades are preferred for their relatively simple operation and accuracy; FIGS. 3-6 below provide a detailed description of a cutting element and cutting head capable of generating an access site having a cross cutting pattern.

A second advantage to cutting an access site having predefined shape and size and predefined edge portion geometry is in the preparation of the site for closure.

As is mentioned hereinabove, prior art approaches for generating access sites do not have control over the geometry of the resultant access site and tissue flaps surrounding it, thus leading to difficulties in subsequent closure, especially in cases where closure is effected via suturing.

It will be appreciated that although the cutting head is described in context of the present system, such a cutting head can also be designed so as to serve as a retrofit option for existing suturing devices. For example, the cutting head can be positioned over a frame which can be fitted over an existing suturing device (e.g. Perclose), or alternatively a frame can be used as a reference for guiding the cutting head and then subsequently and separately guiding a suturing device, thereby generating an access site surrounded by sutures optimally positioned around the edges of the access site cut.

The present system further includes a tissue closure device which serves for attaching one or more closure elements to the tissue at a region corresponding to at least one, preferably all of the tissue edge portions.

The tissue closure element can be a suture, a clip (e.g. a Nitinol wire clip), a patch or a combination thereof. In any case, the closure element is configured for attachment to, the edge portion tissue in a manner which enable subsequent use of the closure element(s) to draw/attach the edge portion together and close the access site.

The tissue closure elements can be attached through the tissue from the inside of the lumen or from the outside. In the case of suture material or Nitinol wires, the closure element can be threaded through the tissue one or several times and drawn out of the tissue through the center access hole, though the side slits defining the edge portions or through the tissue itself. The free end of the suture or wire can then be utilized to manipulate/orient the edge portions so as to draw the edge portions together and ensure a tight closure.

Figure 2:
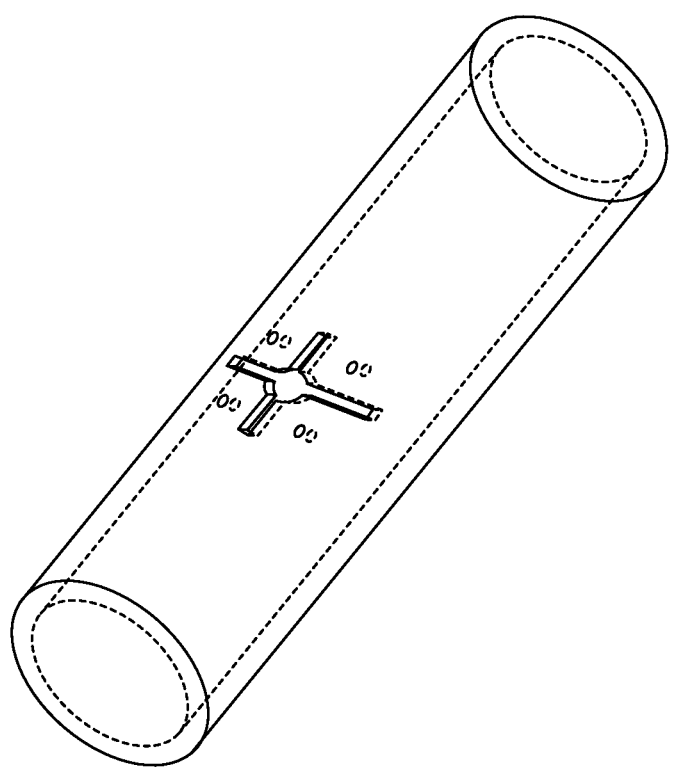
FIG. 2 illustrates the triangular edge portions resulting from a cross shaped cut pattern provided with puncture holes for enabling attachment of tissue attachment elements.

FIG. 2 illustrates exemplary attachment sites (puncture holes) through which closure elements can be attached to or through four triangular edge portions of a cross shaped access site cut. The closure elements in this case can be suture threads that are threaded from the outside of the tissue into the lumen and drawn out of the center hole of the access site.

Attachment of the closure elements can be effected prior to, during or following cutting of the access site.

Figure 7A:
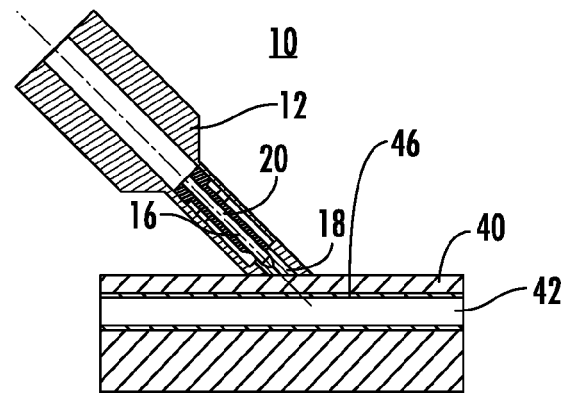
FIGS. 7A-C illustrate closure element attachment to the tissue and subsequent access site generation using the system of the present invention.
Figure 7B:
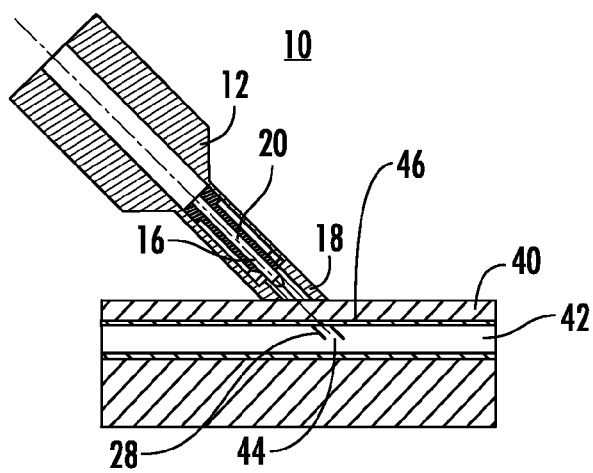
Figure 7C:
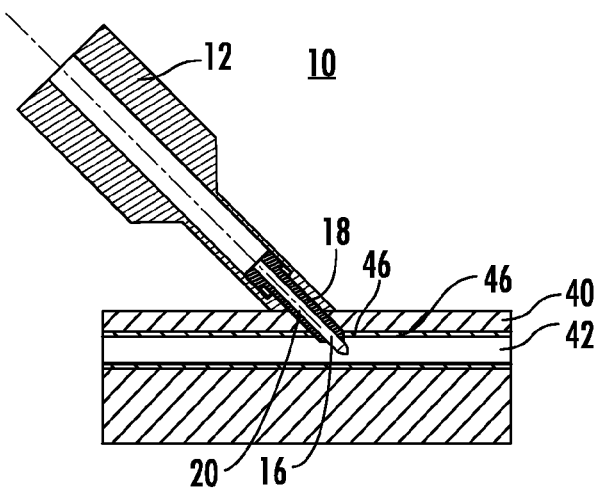

For example, (and as is shown in FIGS. 7a-c), closure elements (e.g. sutures) can be introduced through a site in the tissue (e.g. a wall of a blood vessel) which corresponds to the edge portions formed by a subsequent cut pattern; the free ends of the closure elements can then be positioned within the lumen of the tissue (e.g. lumen of a blood vessel). Following the cut, the closure elements free ends (e.g. suture free ends) can then be captured by a suture drawing element (e.g. suture grabbing hook(s) which can be a part of the present system) and drawn out of the tissue through the access site hole. Attachment of the closure elements prior to tissue cutting is advantageous in that the uncut tissue provides better resistance to the movement of the closure device and thus facilitates piercing of the tissue and introduction of the closure elements therethrough.

Closure elements can also be introduced through the tissue during the cutting of the access site. In such a scenario, the cutting element can be deployed along with the closure device and the cut and closure element attachment can be effected simultaneously to generate a cut pattern with free edge portions which are attached to closure elements. The closure elements can extend from outside the tissue and into the closure site, in which case such elements can be introduced through the overlying tissue (e.g. through the skin and fat layers overlying an artery). Such an approach can be advantageous in that suture type closure elements can be introduced through the skin and underlying tissue and through the tissue surrounding the access site.

It will be appreciated that closure elements can be delivered through the overlying tissue without having to engage such tissue. For example, a suture type closure element can be delivered through the skin and underlying tissue and into the tissue surrounding the access site, a anchoring element (e.g. T-bar or disc) can then be deployed on the trailing end of the suture to act as a backstop against the outer surface of the access site tissue. In such a case the suture is delivered (via, for example, a needle) through the tissue but it is not retained therein, but is rather maintained against the tissue surrounding the access site via a backstop.

In an alternative embodiment, the closure elements can be introduced directly into the tissue of surrounding the access site. In such a case, the cut in the overlying tissue can be used for directly accessing the access site tissue and for attaching closure elements directly thereto without having to deliver the closure elements through the overlying tissue.

Attachment of the closure elements following tissue cutting requires that the free tissue edge portions be stabilized in order to facilitate introduction of the closure elements through the tissue. Such stabilization can be provided by dedicated elements or by the cutting blades which can act to force the tissue edge portions against the force of the closure device. Alternatively, tissue stabilization can be provided by a balloon which is inserted over a guide-wire and inflated within the lumen of the tissue (e.g. lumen of a blood vessel).

FIGS. 3-7 illustrate one specific embodiment of the present system which is configured for generating vascular access sites and preparing such sites for closure.

In this configuration of the present system, the closure elements are sutures/wires which are attached to the tissue around the access site prior to tissue cutting. The sutures/wires are introduced into the tissue (e.g. blood vessel) via needles that are pre-positioned near the intended location of the cut and function in puncturing the tissue and delivering the wires/sutures into the tissue. The present system can include a mechanism which enables to verify that the needles are all in position prior to deployment of the sutures/wires such that they are delivered into the tissue and the suture free ends are positioned so as to enable subsequent capturing and withdrawal from the tissue. For example, in the case of blood vessels, the needles can be deployed into the lumen and checked for blood flow which indicated lumen penetration.

Alternatively, the needles can be preformed such that they curve inward (towards the access site) following delivery into the lumen of the tissue. Such a feature can be enabled by using pre-curved needles or needle guides (e.g. pre-curved Nitinol needles) which are maintained straight in the delivery head and curve inward upon release therefrom or by using a hinging needle assembly.

The cutting element of such a system is configured for creating an arterial access site which can be used for percutaneous procedures. The cut pattern is selected such that it generates an access site which can be used for large bore as well as small bore access with minimal non-elastic deformation to the access site thus enabling the access site tissue to return to its precut position. Closure of the access site is achieved via sutures which are attached to the edge portions of the access site prior to the procedure.

The present system can be deployed at the site of interest (e.g. an arterial wall) through a cut made in the overlying tissue (skin and fat) made by a scalpel. Alternatively, the present system can be deployed against the skin overlying the artery with the cutting head and closure elements delivered through the overlying tissue and arterial wall.

The system described below includes a single housing which integrates both the cutting element and closure device, both separately operable.

FIGS. 3-6 illustrate the present system which is referred to hereinbelow as system 10.

Figure 3:
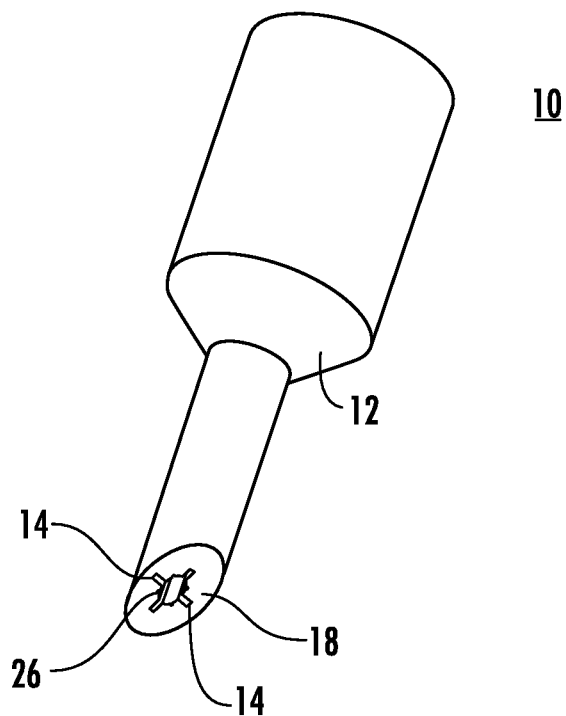
FIG. 3 illustrates the head portion of the system of the present invention showing the blade guides through which the cutting blades are deployed.
Figure 4A:
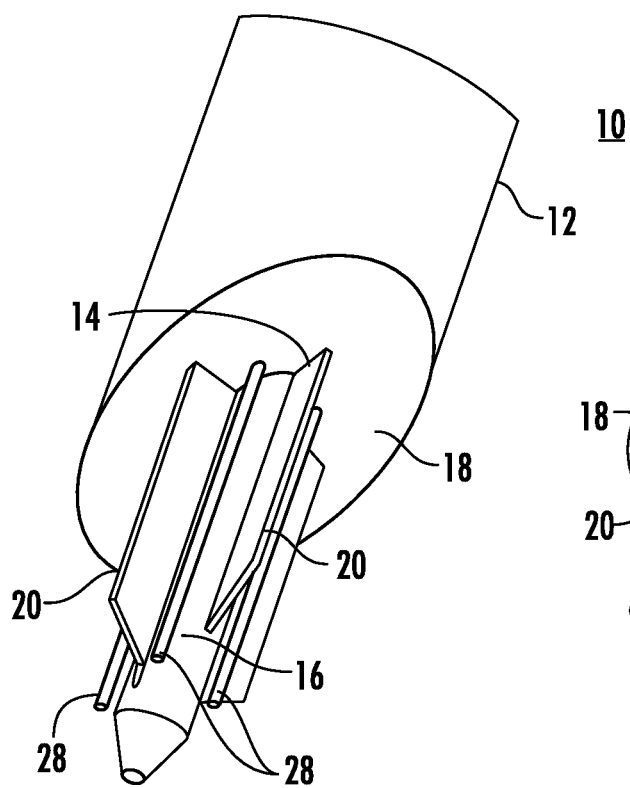
FIGS. 4A-B illustrate the cutting element in a deployed position protruding out of the head portion of the system of the present invention (FIG. 4A is a 10× magnification of the region circled in FIG. 4B).
Figure 4B:
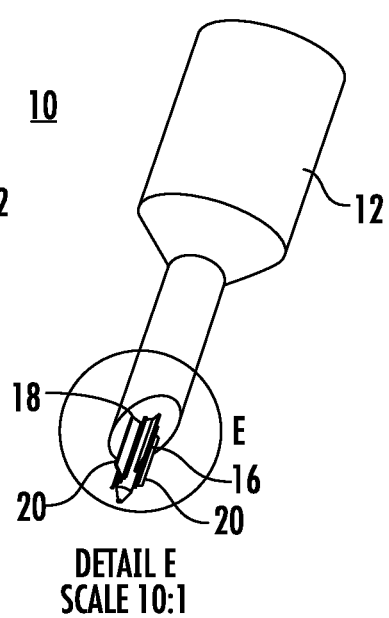
Figure 5:
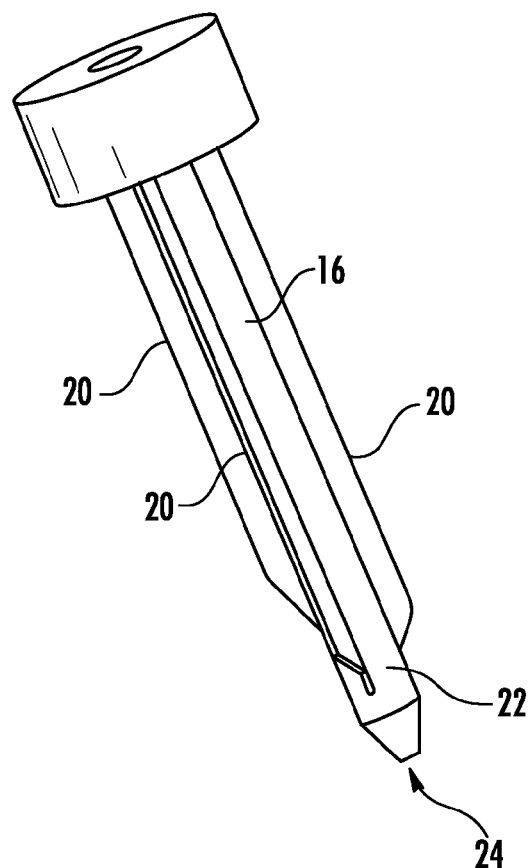
FIG. 5 illustrates the cutting element removed from the housing of the system of the present invention showing the four cutting blades.
Figure 6:
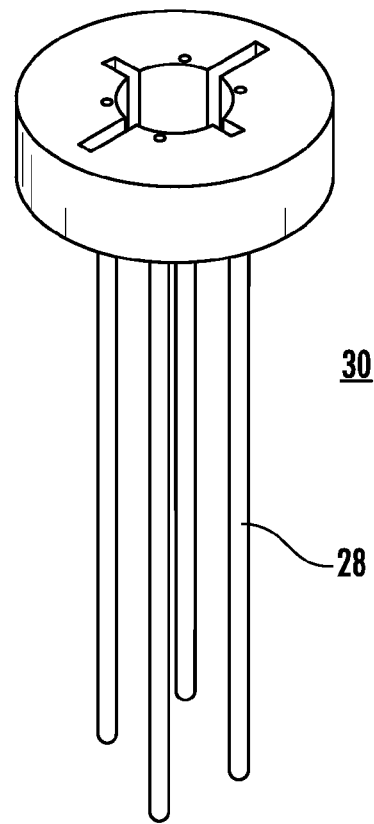
FIG. 6 illustrates the closure device assembly which includes four suture guides.

As is illustrated in FIGS. 3-4b, system 10 includes a housing 12 which includes a shaped cutting element tract 14 for guiding the movement of a shaped cutting element 16 (shown in FIGS. 4a-5) out of and into housing 12. A cross shaped cutting blade and tract are illustrated in FIGS. 4a-5; other configurations can include a straight blade, a v-shaped blade as well a three flange blade or any configuration suitable for creating a controlled cut in the tissue. Housing 12 can be molded or machined from a metal (e.g. stainless steel) or a polymer (e.g. polypropylene) a combination thereof using techniques well known to the ordinary skilled artisan.

Cutting element 16 moves along tract 14 and out of housing 12 to cut a cross-shaped pattern through the tissue. Head portion 18 of housing 12 is angled (30-60 degrees) in order to provide an angle of operation with respect to the tissue. Cutting element 16 moves out of head portion 18, to a position in which blades 20 of cutting element 16 are capable of cutting through a wall of an artery while not damaging the interior walls of the blood vessel.

FIG. 5 illustrates cutting element 16 out of housing 12. The cross shape cutting element includes four blades that move as a single unit although configurations in which each of the blades move separately are also envisaged.

The preferred cutting angle is 45°. Cutting blades 20 drive through a stroke which is limited by a stopper in housing 12 or disposed on blades 20. The stroke is determined and adjusted according to the tissue treated. In the case of arteries it is typically between 10 and 20 mm. In case of a simple straight cut or a V cut the cut is made by a single blade structure (that can be constructed from one or two blades). This type of cut will be perpendicular to the lumen axis. The length of a straight cut would normally be 4-8 mm; the thickness of the blades is normally ~0.1 mm. In the more complex configurations, e.g. cross shaped blades, non-symmetric blades can be used such that a symmetric cut is formed when used in a 45 degree cutting angle.

Blades 20 of cutting element 16 are arranged around a central rod 22 which also includes a central bore 24 which can run the length of housing 12 and is designed for receiving a guide-wire or needle. The needle and/or guide-wire can be used for initial positioning of System 10 against the blood vessel as is further described hereinbelow with respect to FIGS. 7a-c.

Housing 12 also includes channels 26 for guiding tubes 28 which form a part of closure device 30 (shown in FIG. 6). tubes 28 are designed for ejection out of channels 26 of housing 12 and penetration through the arterial wall. Such ejection can be provided via triggered spring elements or ejection arms.

System 10 further includes proximal handles and connecting arms (not shown) for separately operating cutting element 16 and closure device 30. The handles can be compressed to push cutting element 16 and tubes 28 out of housing 12 and against the wall of the artery. Closure device 30 and/or cutting element 16 may further include a safety mechanism to prevent premature operation. System 10 may further include a locking mechanism for preventing cutting element 16 and/or closure device 30 from being advanced past a predetermined point. This mechanism ensures that cutting element 16 and/or closure device 30 do not accidentally damage internal arterial tissue.

Closure elements formed as wires composed of a metallic, preferably Nitinol head (wire leader) and a metallic or polymeric suture/wire/thread (wire tail) are preloaded into tubes 28 (one wire/suture per tube 28). The wire leader may include a tissue piercing head for penetrating through tissue or such tissue piercing can be effected by tubes 28. The wire leader further includes an engaging feature (e.g. small hook) which is designed for engaging a receiver element which can be positioned on central rod 22 or blades 20 of cutting element 16.

Such a receiver (not shown) can be a mesh configured for engaging the wire leader within the lumen of the artery or a hook configured for grabbing the wire tail and drawing it out through the access site formed by cutting element 16. The mesh or hook can be deployable from central rod 22 to expand in order to engage the wire leader. For example, a mesh structure can be sequestered (compressed) within central rod 22 and expanded (much the same as a stent) to form a net like structure which can trap the wire leader which can be provided with a hook or a ball-like protrusion. Following trapping of the wire leader the mesh and attached wires can be retracted and withdrawn out of the access site.

In the case where 4 wires are utilized, the wire tail can terminate in a T-bar or disc-shaped anchoring element which functions as a backstop against the skin or the outside wall of the artery. Such an anchoring element can be preloaded into channels 16 along with the wire and suture. The anchoring element can be forced out of tube 28 via a pushrod provided therein or simply by pulling on the free ends of the wires (withdrawn through the access site). In cases where the wires are delivered through overlying tissue, the anchoring element can be secured against such overlying tissue (e.g. skin), or delivered through the overlying tissue and deployed against the tissue surrounding the access site (e.g. outer arterial wall).

When two wires are utilized, i.e. loaded into the four tubes 28, such that each pair of tubes 28 carries a single looped wire (with the loop end sequestered within housing 12), the free ends of the wires are delivered into the tissue and recovered as is described above with loop of each wire functioning as a 'backstop'.

FIGS. 7a-c illustrate the operation of system 10 against an artery 40.

An artery such as a femoral artery is exposed using a minimal tissue cut and a needle is driven through the arterial wall at a 45 degree angle to create a hole for inserting a guide-wire into the lumen 42 of the artery. Accurate placement of the needle is indicated by blood flow out of the needle bore (not shown). A guide-wire 44 is inserted into the artery through the needle bore and the needle is removed.

Housing 12 of system 10 is mounted over guide-wire 44 (shown in FIG. 7b) and system 10 is positioned through the tissue and over an outside surface of wall 46 of artery 40 such that head portion 18 of housing 12 fully contacts wall 46 and housing is angled with respect to artery 40 at approximately 45 degrees.

Tubes 28 (not shown) are moved into position against wall 46 and the wires are forced through wall 46 and into lumen 42 of artery 40 such that the wire leader is disposed within the artery while the tail portion protrudes out of the arterial wall with the backstop still maintained within channels 26 of housing 12.

With the wire leaders disposed within lumen 42, cutting element 16 is deployed (pushed out of tract 14 within housing 12) through wall 46 to create a cross-shaped cut through the tissue. Blades 20 or central rod 22 which are now disposed within lumen 48 of artery 40 engage the wire leaders within lumen 42 of artery 40. Retracting cutting element 16 back into housing 12 pulls the wires out of lumen 42 through the tissue cut. Further retraction of cutting element out of the formed access site and/or retraction of housing 12 out of the tissue further pulls wires out of the tissue cut and frees the wire tail (and included backstop) from tubes 28.

Complete withdrawal of housing 12 out of the body pulls out the head portion of the wires outside the body and secures backstop against outside surface of wall 46.

System 10 can now be completely removed leaving behind a cross-shaped cut having triangular edge portion each fitted with a wire suture going into the artery at the edge portion and out through the center of the incision. The wires may be individually color coded to allow identification of each with respect to its position around the access site.

A working sheath can then be inserted through the cut tissue by forcing the edge portions and attached wires inwardly into lumen 48. A procedure, such as abdominal aortic Aneurysm (AAA) or percutaneous valve replacement (e.g. AVR) can then be performed through the sheath. Throughout the procedure, the free leader portions of the wires are maintained outside the body (e.g. taped against the skin around the skin incision).

Following the procedure, the sheath is pulled out and edge portion are allowed to retract back up to partially close the access site. The wires are then utilized to close the access site and prevent leakage of blood therethrough.

Several closure schemes can be utilized. Since the wires exit lumen 48 through the center of the access site from the center of the incision, one or more securing elements (e.g. tie rings, clips or patches) can be pushed along the wires from outside the body and against the arterial wall 46. The securing element(s) can secure the wires via friction adhesive and the like, or alternatively, the wires can be knotted over the securing element(s). In any case, the wires are secured such that the edge portions are forced against each other and around the cut. Compression is applied to the sutures (and therefore the cut site) until leakage is no longer detected and then the wires are secured via the securing element and the ends are cut and removed from the tissue.

Such securing elements can be used to secure the wires into a single bundle or to secure pairs of the wires. In any case, the securing element is pushed over the wire from outside the body and up against the arterial wall. Pushing can be effected with a dedicated tool with a distal end configured for holding the securing element(s), moving it along the wires and releasing it at the site of the arterial wall.

An advantage of such securing element is that it prevents the wires from applying excessive pulling forces on the tissue when the access site is closed.

The securing element can be a clip for clipping together the wires or a button. The clip/button can be fabricated from a bio-absorbable material such as a polymer composed of polyglycolic and/or polylactic acid units (e.g. PGA, PLA or PLGA).

Figure 19:
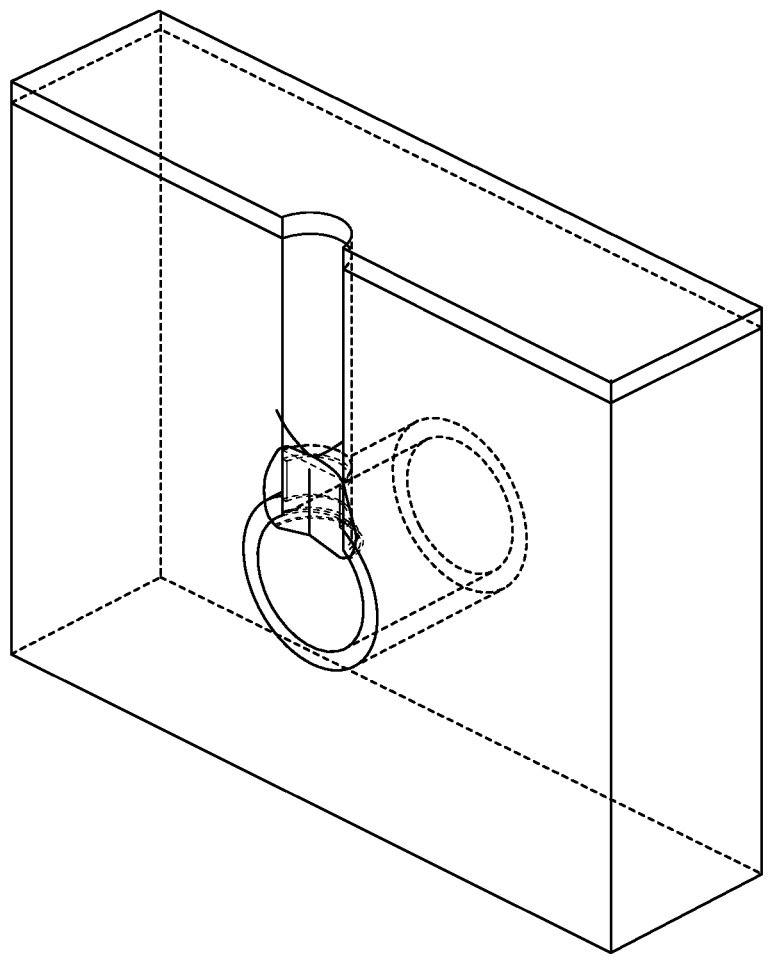
FIG. 19 illustrates one embodiment of a securing element constructed in accordance with the teachings of the present invention.

One example of securing element is shown in FIG. 19. As is illustrated in this Figure, the securing element is disposed within the access site while the first ends of the wires/sutures are co-threaded through a central hole of the securing element and the second ends are looped above the securing element or attached thereto (prior to, or following positioning of the securing element).

This exemplified configuration of a securing element is disc shaped and includes a central hole for accepting the ends of the wires/sutures utilized for closure. The securing element of FIG. 19 is designed for placement within the access site such that the tissue edges of the access site abut the circumference of the securing element. The disc can be designed such that the tissue edges abutting its circumference fit within a circumferential slot (e.g. grommet shaped). A securing element that functions as a plug (rather than a patch) provides a tighter seal while reducing the forces of the sutures/wires on the tissue during closure.

This configuration of the securing element can be used as follows, the end of the sutures (4-6 sutures) coming out of the access site, are threaded through the center hole of the securing element. The center hole can then be crimped (plastic deformation) to hold the sutures together while the proximal ends (coming out of the center hole) are cut or are tied together.

The opposing suture ends are gently pulled (in a proximal direction) and the element is advanced (pushed from the top and pulled by the sutures) into the access site to a point where the securing element engages the tissue around the access site. Once the element is in place the sutures ends that were pulled are tied to each other above the element to achieve tight contact of artery tissue and the closure element while sutures ends are cut proximally to knot.

Although withdrawal of the wires through the cut site is preferred, other configurations of system 10 in which the wires are stitched through the tissue are also envisaged. In such cases, the closure device includes a stitching head which enables threading of the wires into and out of the arterial wall. For example, a stitching head having curved needles which penetrate the arterial wall from the outside and curve back out can be used to thread one or more wires around the access site.

It will be appreciated that the present system can also be utilized to reduce the access site size (to, for example, 6-8F) rather than completely close it. In such cases less suturing is requires (e.g. two stitches on in each 'arm' of a V-shaped access site cut) and complete closure can be effected via a sealant, an adhesive or a patch/sponge/plug or the like which can be administered using the present system or a separate device (e.g. tissue adhesive dispenser).

Thus, the present invention provides a system for access site generation and closure. The present system provides several advantages over prior art approaches including:

(i) known cut geometry minimizes distortion/tearing of the access site during dilation and procedure;

(ii) enables accurate closure since the suture is placed accurately with respect to the cut and since multiple sutures are placed with accuracy with respect to one another; and (iii) reduces residual narrowing of the lumen at the closure site;

(iv) Reduces risk of sutures misplacement (sutures that do not grab tissue or grab minimal tissue portions);

(v) Securing element reduces forces of sutures on tissue and maintains force symmetry—minimizes risk of suture tearing through tissue.

The present invention also encompasses a system which combines the functions of a dilator and a closure device.

Thus, according to another aspect of the present invention, the closure device described above is integrated with the function of a dilator such that closure elements are attached to the tissue surrounding a hole (e.g. a needle puncture) prior to or during dilation of the hole to generate an access site.

Such a system integrates (preferably in a single housing) a tissue dilating element which is designed for dilating a hole in a tissue (e.g. a conically shaped, guide-wire guided dilator sheath) with the tissue closure device described herein.

Figure 16:
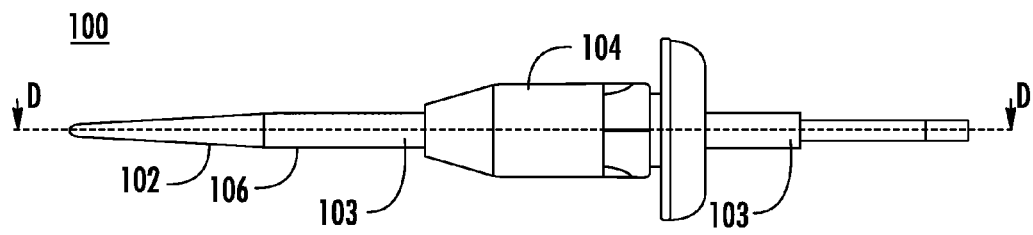
FIGS. 16, 17 and 18 illustrate an embodiment of a system incorporating dilator and suture closure functions.
Figure 17:
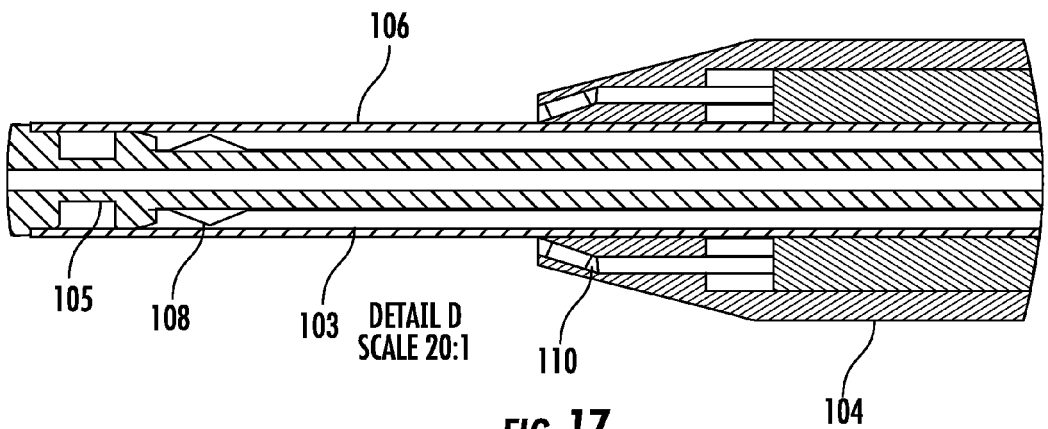
Figure 18:
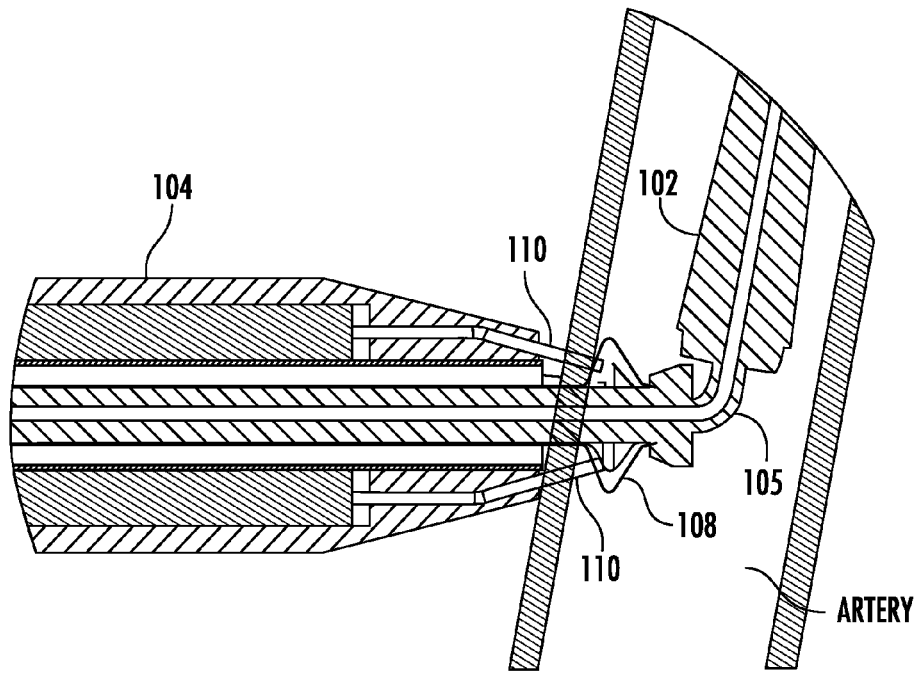

FIGS. 16-18 illustrate a system for dilating and suturing an access site which is referred to herein as system 100.

System 100 includes a dilator portion 102 which is hingedly attached to a central shaft 103 (via hinge 105) which runs through a stitching portion 104 (which can be translated along central shaft 103). Central shaft 103 includes a collector 108 which is configured for actuation between open (radially expanded, FIG. 18) and closed (radially collapsed, FIG. 17) positions. Stitching portion 104 and part of dilator portion 102 are covered by sheath 106 which when pulled back (proximally) exposes a hinge portion 105 which enables articulation of dilator portion 102 with respect to central shaft 103 and stitching portion 104. This articulation enables positioning of stitching portion 104 at the access site while dilator portion is positioned within and along the artery. Stitching portion 104 includes needle guides 110 (containing needle pushrods) which are exposed and deployed when sheath 106 is pulled back to the open position. Needles guides 110 and contained pushrods are configured for delivering needles and attached sutures through the arterial wall and into the artery lumen. Collector 108 is configured for capturing needles and attached sutures when in the open position. Once needles and attached sutures are delivered and captured, sheath 106 is closed to actuate collector 108 to the closed (collapsed) position and to thereby retain the sutures.

System 100 is utilized as follows, the artery is exposed and punctured with a needle or a cutting element 16. A guide wire is inserted into the artery and a dilator portion 102 of system 100 is positioned over the wire and utilized to dilate the access site to a size of about 12F. Stitching portion 104 is then pushed along central shaft 103 up against the access site and sheath 106 is pulled back to open collector 108 (mounted on central shaft 103 and positioned within the lumen of the artery) and allow angulation (70-90 degrees) between dilator portion 102 and stitching portion 104. System 100 is pulled back until collector 108 is juxtaposed against the inner wall of the artery, such that collector 108 pushes against the inner artery wall around the access site. Needle guides 110 are then deployed and the pushrods are utilized to drive needles (and attached sutures) through the artery wall and into collector 108.

The needles will penetrate the artery wall in predefined angle and will engage collector 108 at a predefined location (see FIG. 18). Needle guides 110 are then pulled back leaving the needles and attached sutures attached to collector 108. Sheath 106 is then pushed to a closed position to close collector 108 thereby locking the needles and attached sutures to central shaft 103.

System 100 is then optionally further advanced into artery (about 100-200 mm) to extend suture length into the artery to prevent trapping of suture thread at the access site. Stitching portion 104 remains in position while central shaft 103 and attached dilator portion 102 are pulled out through the center of stitching portion 104 and out of the body. Removal of central shaft 103 pulls the sutures ends attached to collector 108 through the access site and out of the body, the suture ends can then be released from collector 108. The stitching portion is then removed and a catheter can then be positioned over the wire and advanced through the access site and used in a medical procedure. Once the medical procedure is completed, the suture ends disposed outside the body can be used to close the access site as described above.

It will be appreciated that although the system described above is advantageous in that it enables preparation of an access site for subsequent closure or reduction, an access site, whether generated using the controlled cutting element of the present invention or not, can also be reduced or closed via alternative approaches.

Thus, according to another aspect of the present invention there is provided a system and method for closure of an arterial access site using a contra lateral closure component. As is further described below, such a contra lateral closure device preferably functions cooperatively with an ipsi lateral device. However, it will be appreciated that use of the contra lateral component alone is also envisaged herein.

Closure of a tissue access site using a system which includes a contra lateral device and an ipsi lateral device is illustrated in FIGS. 20-25. Briefly, the ipsi-lateral component includes an 18 G needle and a 350 micron guide-wire, as well as a dilation kit which includes a set of 12 to 24fr dilators and a 24F introducer/sheath with a depth marker and a 14-18F flex guide/sheath with shaped tip. The tip is configured for enabling passing of the contra-lateral guide-wire over the ipsi-lateral guide-wire (and co-positioning of both) and is typically shaped as a soft (elastic) conic snub nose tip about 50-75 mm in length with a distal diameter of about 1-3 mm, and a proximal diameter of about 6-18 mm. The tip can also include channels/grooves along the length thereof for further facilitating passage of the contra-lateral guide-wire.

The contra-lateral component includes a needle and guide wire (standard) and a deployable tubular element which is 4-5F in a folded configuration and 22-28F in an open (deployable) configuration. The tubular element is typically 20-30 mm long and is configured as a rolled up sheet, a wire mesh with a partial or a complete cover, or a tube with solid walls composed of a biodegradable material. The contra-lateral component further includes a 6F guide catheter with pre-shaped tip and external 24-28F compliant balloon (silicone) and an optional small hole closure device (Standard).

Figure 20:
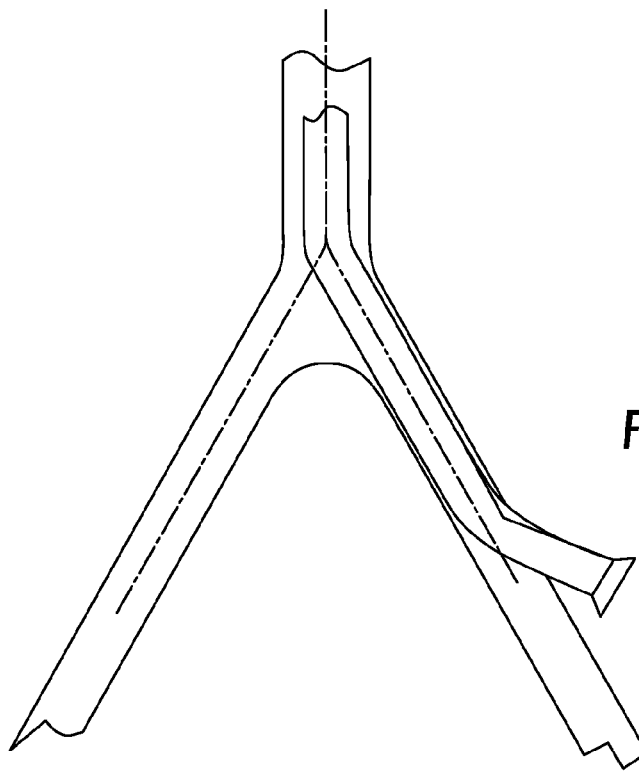
FIGS. 20, 21, 22, 23, 24 and 25 illustrate use of the contra lateral system of the present invention in closure of an arterial access site.

The present system can be used with a 22-28F sheath with/without the pre-procedure controlled cut (FIG. 20).

Once the procedure is done, an access from the ipsi-lateral side is achieved (using known approaches), a guide-wire is inserted to the ipsi iliac and a 6F guide catheter is placed over the guide-wire while the 22-28F sheath and wire are pulled to mid iliac.

Figure 21:
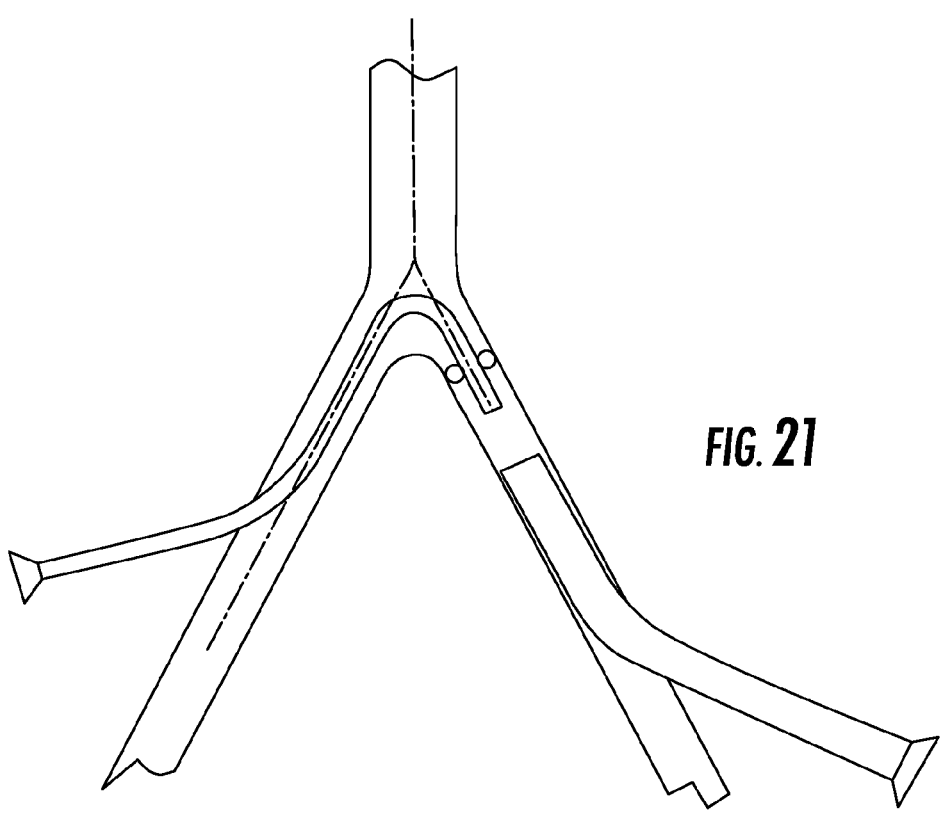

Once the guide catheter is located in the ipsi-lateral iliac distal end a safety occlusion is performed by inflating the 22-28F element/balloon (FIG. 21).

Figure 22:
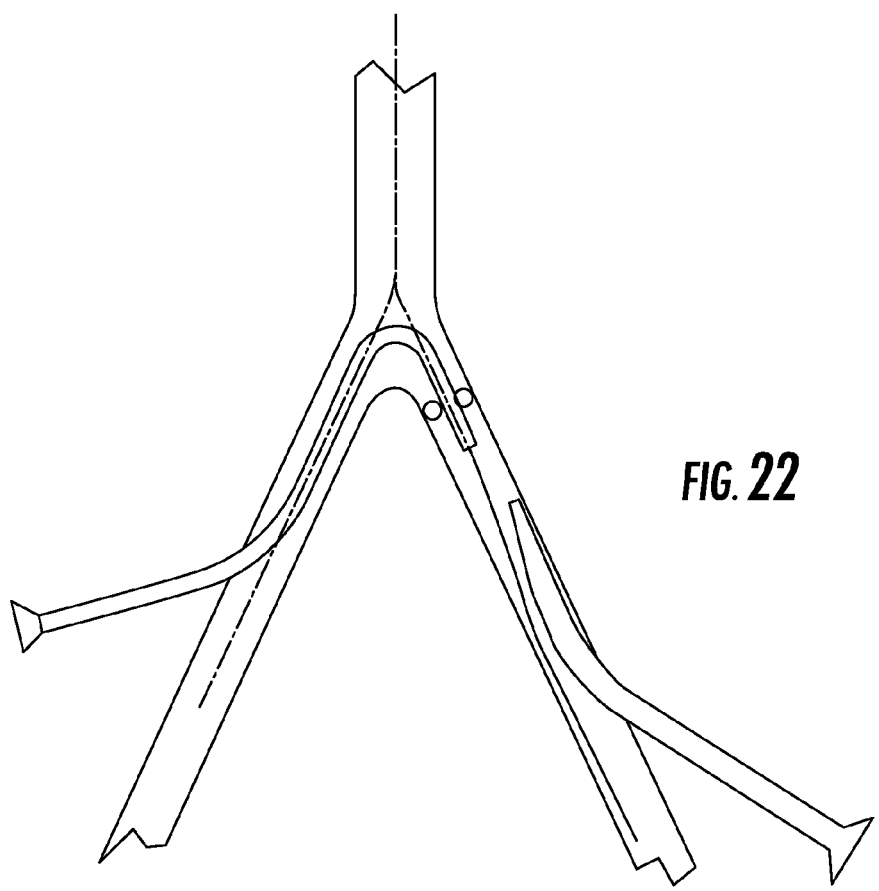

The 22-28F ipsi-lateral sheath is then fully retracted and the 14-18F sheath (with the special tip described above) is guided over the ipsi-lateral guide-wire back to mid iliac to allow the contra-lateral guide-wire to progress down over the ipsi-lateral access site hole (FIG. 22).

Figure 23:
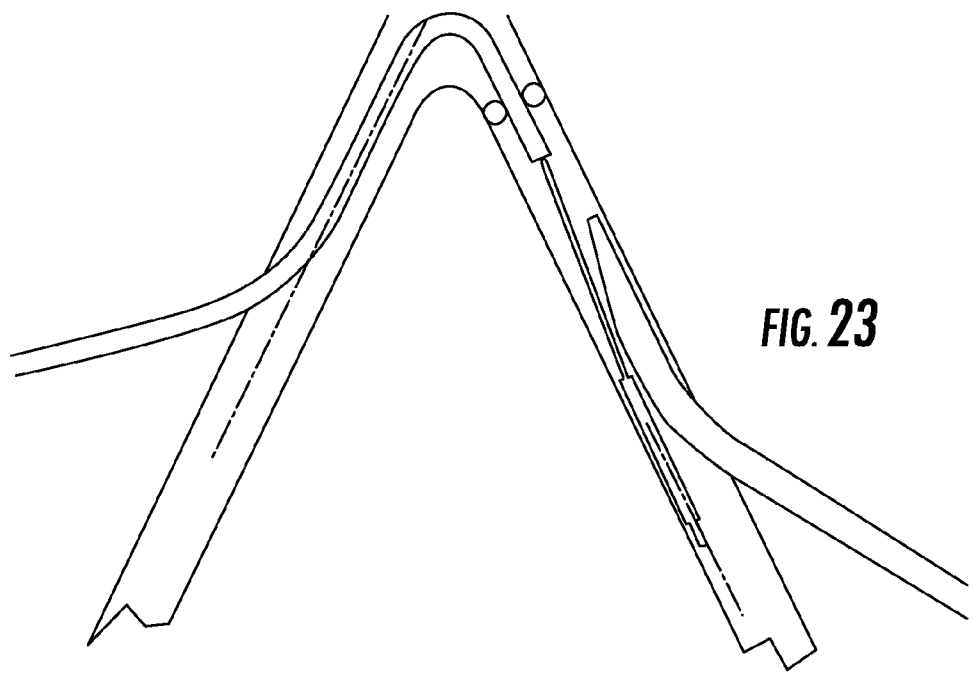
Figure 24:
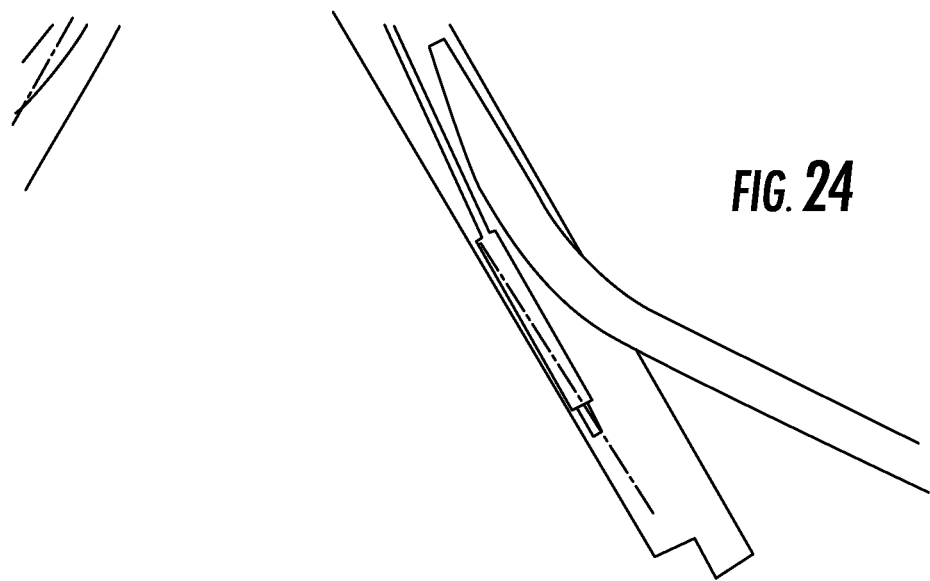

Once the contra-lateral guide-wire is in location, a folded tubular element (e.g. wire tubular element with a polymeric or tissue cover) is inserted from the contra-lateral access site over the contra-lateral guide-wire to be located over ipsi access hole (FIGS. 23-24). All the above steps are preformed while monitoring and adjusting the blood flow using the balloon occlusion.

Figure 25:
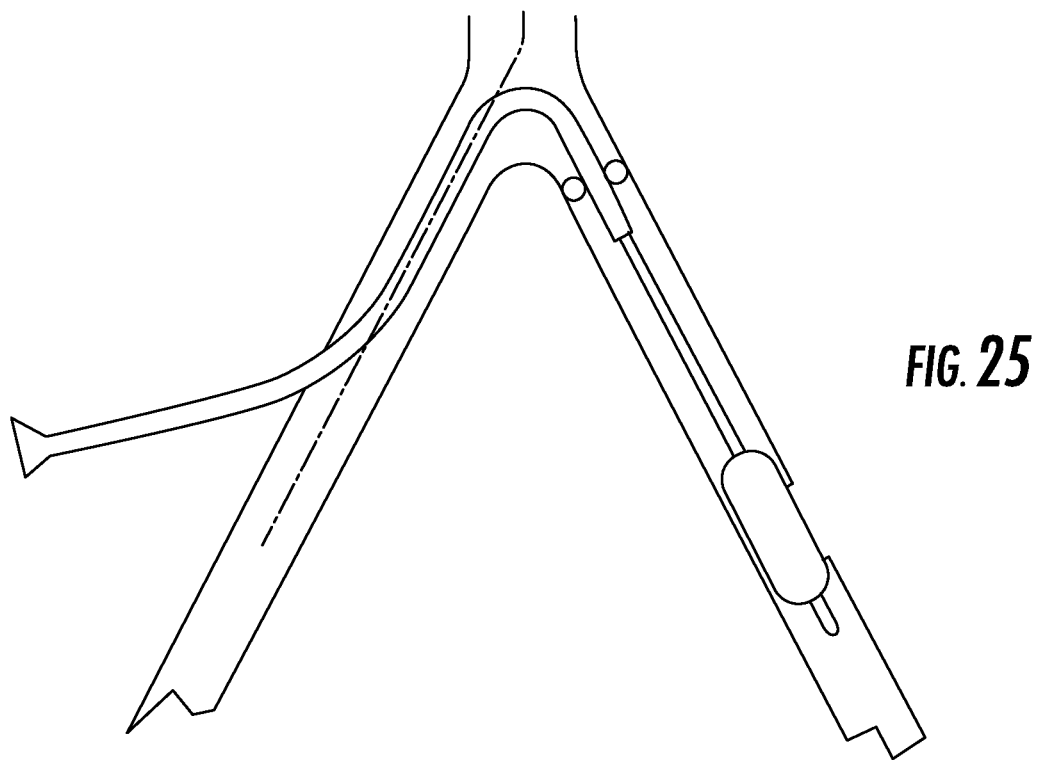

The 14-18F flex sheath is removed and the graft position across the hole is verified. The graft is then deployed (via inflation or release mechanisms—similar to those utilized in stents or stent grafts) and the integrity of the closure is verified by checking for blood leaks from the ipsi-lateral access site (FIG. 25).

The contra-lateral catheter and guide catheter are then removed along with the wire and the contra-lateral access site is closed using any one of several known approaches. The ipsi-lateral access site hole can then be closed using sutures, patch, an adhesive or the like.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLE

Reference is now made to the following example, which together with the above descriptions, illustrate the invention in a non limiting fashion.

A phantom model was used to simulate access site generation and closure. A silicon tube 50 (OD 9 mm, ID 7 mm) was wrapped with raw chicken breast tissue 51 and a jig 52 for guiding needles and cutting blades was used to simulate the operating head of the present system. The jig 52 was machined from aluminum as a round disc 54 having a 45 degree tissue interface angle and a cross shaped slot 56 and four holes 58 for guiding the blades and needles respectively (see FIGS. 8a-b and 9a-c).

Figure 8A:
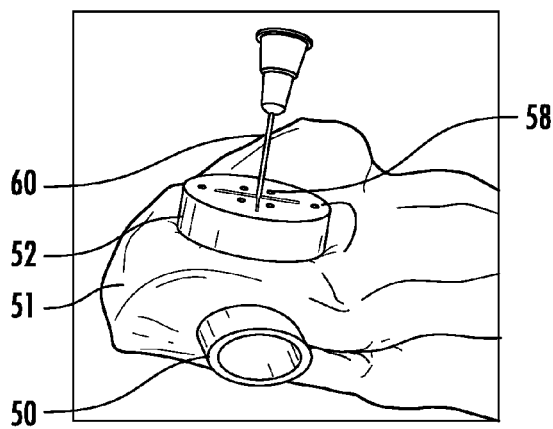
FIGS. 8A-B, 9A-C, 10A-C, 11A-B, 12A-E, 13A-C, 14A-d and 15A-B illustrate access site generation and closure according to the teachings of the present invention as demonstrated on a phantom model simulating a tissue-embedded blood vessel.
Figure 8B:
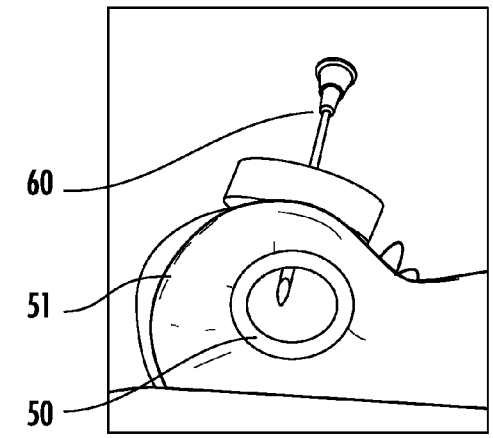

In the first step, illustrated in FIGS. 8a-b, a needle 60 was inserted through the tissue 51 and silicone tube 50 at a 45 degree angle as guided by the jig 52. A guide-wire can then be inserted through the needle into the lumen of the silicone tube 50. The guide-wire can then be used to guide the system through suture insertion and cutting. Since in the phantom model a jig is used to simulate the operational head of the present system, use of a guide-wire is not needed.

Figure 9A:
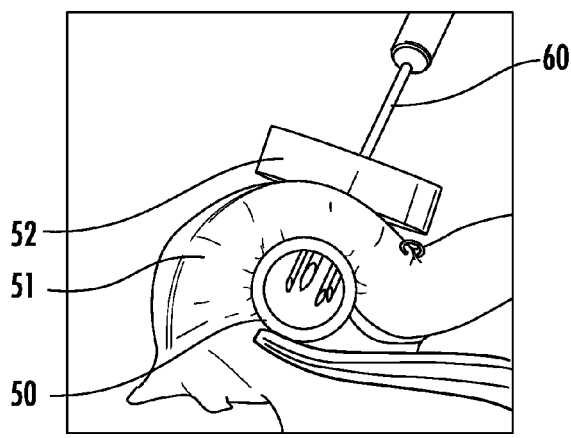
Figure 9B:
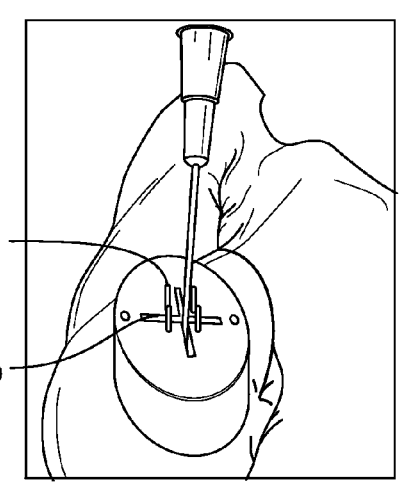
Figure 9C:
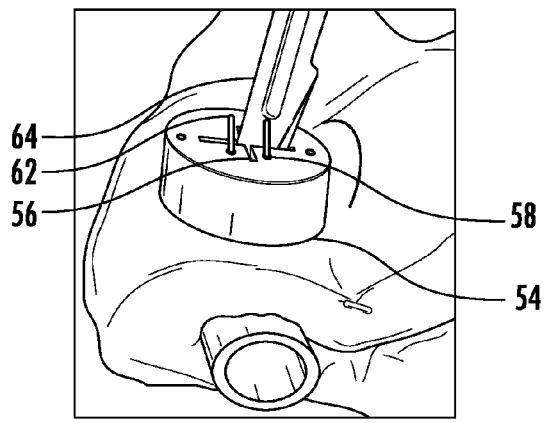

The suture needles 62 were then inserted through the tissue 51 and into the lumen of the silicone tube 50 (FIGS. 9a-b) and a cutting blade 64 was utilized to cut a straight radial cut pattern in the silicon tube wall to generate the access site (FIG. 9c).

Figures 10A, 10B:
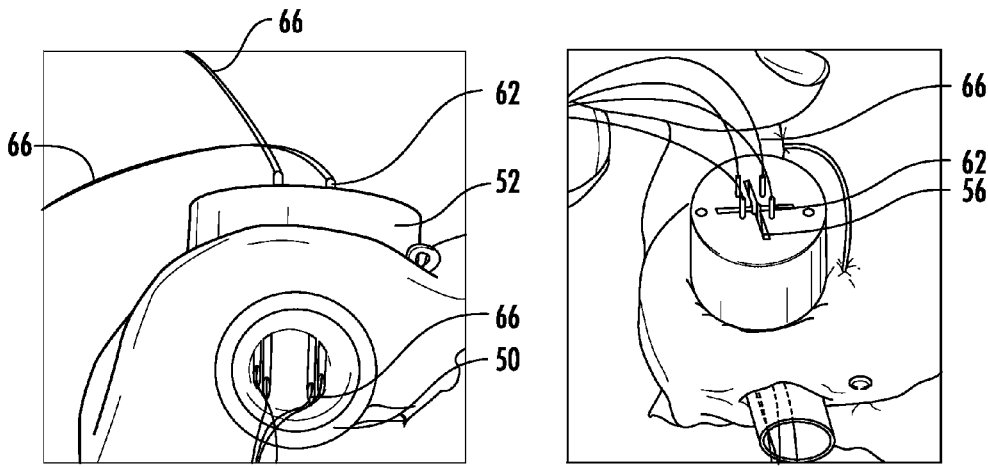
Figure 10C:
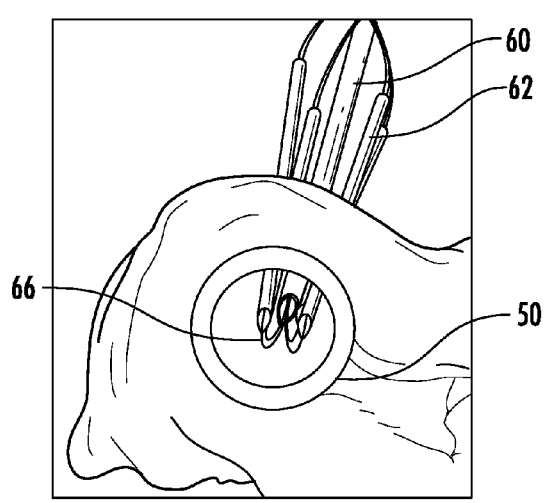

Sutures (4-0) 66 were then threaded through the four needles 62 and into the lumen of the silicon tube 50 (FIGS. 10a-c).

Figures 11A, 11B:
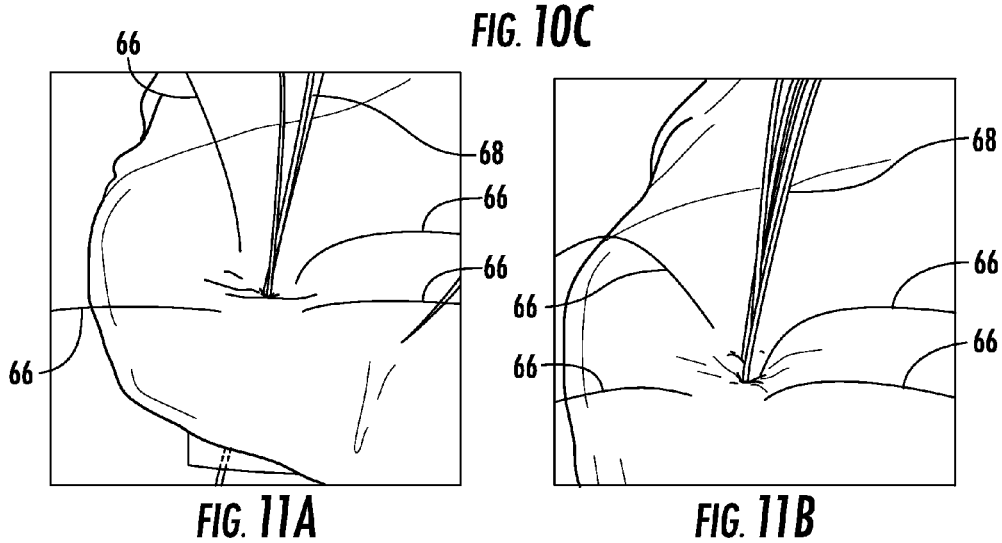
Figure 12A:
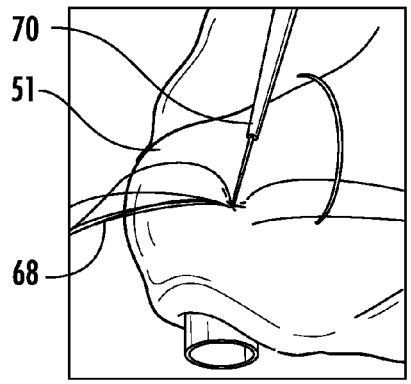
Figure 12B:
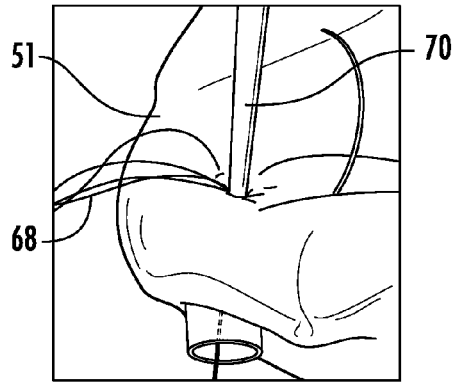
Figure 12C:
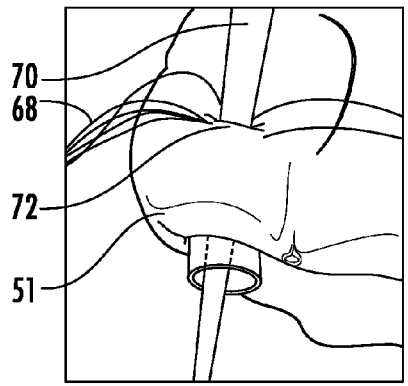
Figure 12D:
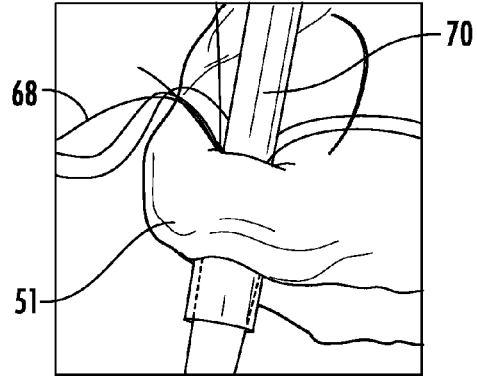
Figure 12E:
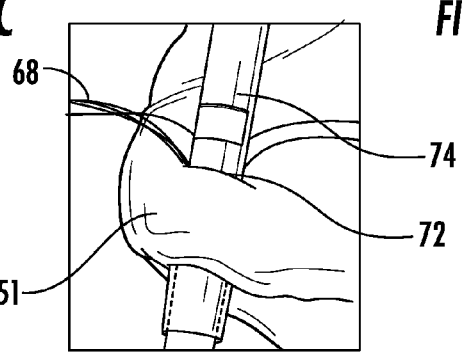
Figure 13A:
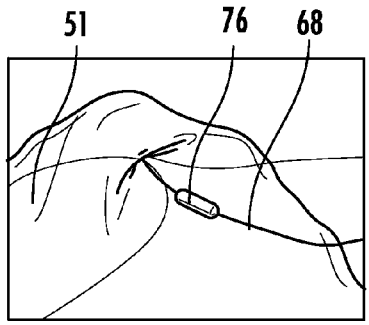
Figure 13B:
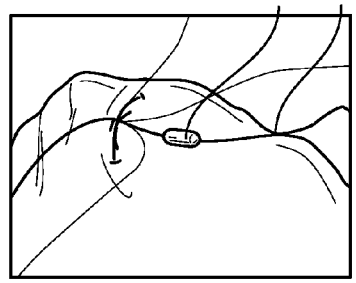
Figure 13C:
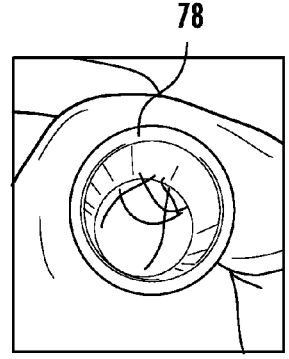
Figure 14A:
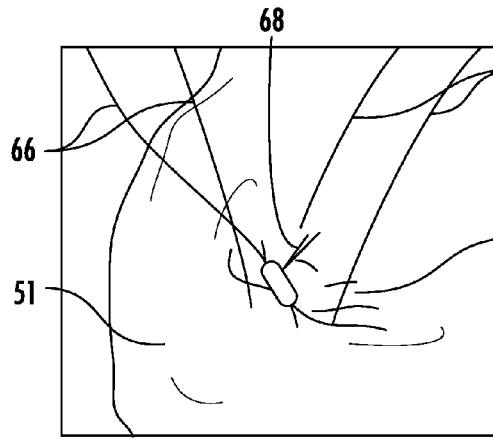
Figure 14B:
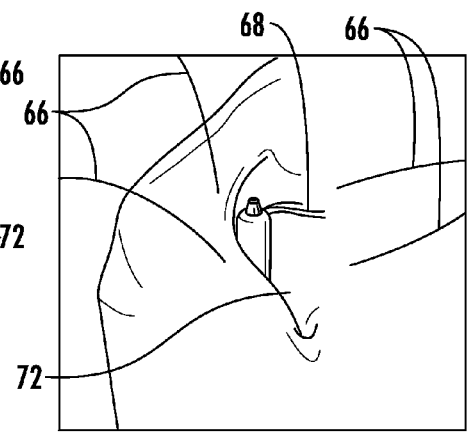
Figure 14C:
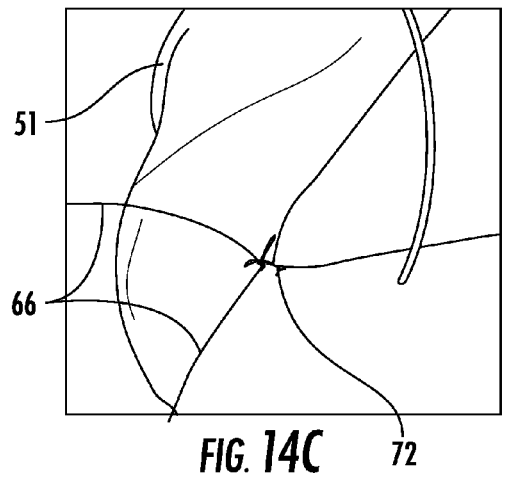
Figure 14D:
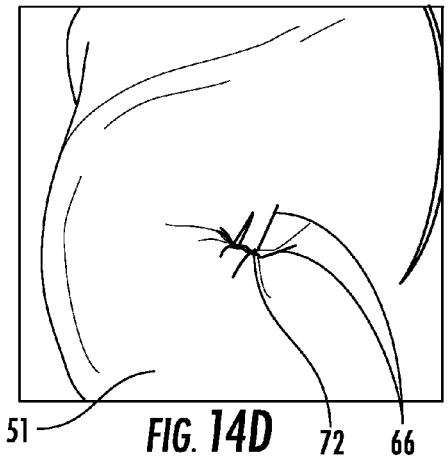
Figure 15A:
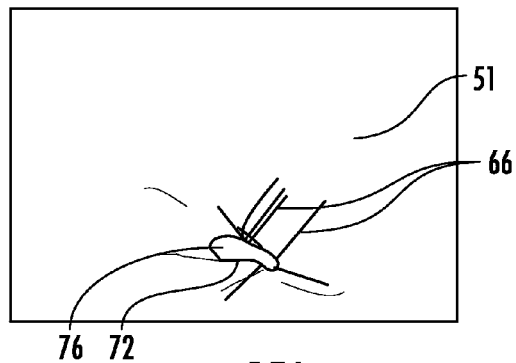
Figure 15B:
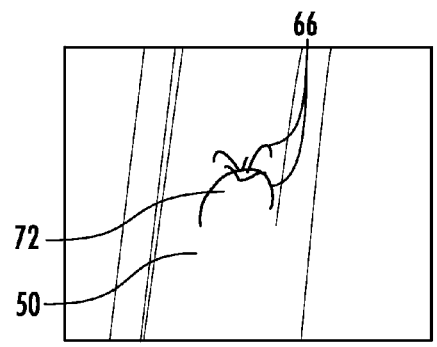

The free ends 68 of the sutures 66 were captured within the lumen and withdrawn from the silicone tube 50 and tissue 51 through the central needle 60 and the jig 52 was removed while the sutures 66 remained in the tube 50 and tissue 51 (FIGS. 11a-b). A dilator 70 was then inserted between the suture ends 68 and through the tissue 51 and access site 72 in the silicone tube 50 (FIGS. 12a-e), such dilation does not appreciably deform the cut site or surrounding silicone. Following access site dilation, a tube 74 simulating a 22F working sheath (shown in FIG. 12e) was inserted through the access site 72. To close the access site 72, the suture central ends 68 where pulled out and a bead 76 (acting as a clip) was threaded along the 4 sutures 66 down through the tissue 51 and up against the silicon tube outer wall 78. The free ends 68 of the sutures 66 (protruding from the tissue 51) were drawn tight and tied and the access site 72 closed (FIGS. 14a-d). FIGS. 15a-b show the resultant external (FIG. 15a) and internal closure (FIG. 15b).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A tissue access site system comprising:
a tissue cutting element comprising a central rod and a plurality of blades positioned in a circumferential array around the central rod, each of the plurality of blades extending radially from the central rod, wherein the blades and the central rod are configured to be jointly penetrated through a tissue wall to generate a tissue access site configured to accommodate insertion of a medical instrument or a sheath through which a medical instrument can be deployed, and wherein the tissue access site is defined by a plurality of tissue flaps having a predetermined geometry; and
a tissue closure device comprising a plurality of tubes positioned in a circumferential array about an axis of the tissue closure device, wherein each tube contains a suture therein, wherein the tubes are configured for attaching the sutures to the tissue wall at locations corresponding to each of the tissue flaps, and wherein each blade is positioned circumferentially between adjacent tubes.

2. The tissue access site system of claim 1, wherein each blade extends radially outward beyond adjacent tubes.

3. The tissue access site system of claim 1, wherein the tissue cutting element and the tissue closure device are coaxial with one another.

4. The tissue access site system of claim 3, wherein the tissue cutting element and the tissue closure device are configured to translate axially with respect to one another.

5. The tissue access site system of claim 3, wherein the tissue cutting element and the tissue closure device are rotationally keyed to one another.

6. The tissue access site system of claim 1, wherein the blades are configured for generating a cross-shaped tissue access site such that the tissue flaps have a triangular shape.

7. The tissue access site system of claim 1, wherein the blades are configured for generating the tissue access site upon entering the tissue wall.

8. The tissue access site system of claim 1, wherein the blades are configured for generating the tissue access site upon exiting the tissue wall.

9. The tissue access site system of claim 1, further comprising a housing configured for guiding the tissue cutting element and the tissue closure device toward the tissue wall.

10. The tissue access site system of claim 9, wherein the housing comprises a plurality of cutting element tracts configured for guiding the blades toward the tissue wall.

11. The tissue access site system of claim 9, wherein the housing comprises a plurality of channels configured for guiding the tubes toward the tissue wall.

12. The tissue access site system of claim 9, wherein the tissue cutting element and the tissue closure device are configured for being separately deployed from the housing.

13. The tissue access site system of claim 9, wherein the tissue cutting element is configured for moving from a storage position in which the central rod and the blades are positioned within the housing to a deployed position in which the central rod and the blades extend out of the housing.

14. The tissue access site system of claim 9, wherein the tissue closure device is configured for moving from a storage position in which the tubes are positioned within the housing to a deployed position in which the tubes extend out of the housing.

15. The tissue access site system of claim 1, wherein the plurality of blades are fixedly attached to the central rod.

16. The tissue access site system of claim 15, further comprising a housing having a channel configured to accommodate the tissue cutting element and sliding motion of the tissue cutting element therein.

17. A tissue access site system comprising:
a tissue cutting element comprising a central rod and at least one blade positioned about an axis of the central rod, each of the at least one blade extending radially from the central rod, wherein the at least one blade and the central rod are configured to be jointly penetrated through a tissue wall to generate a tissue access site configured to accommodate insertion of a medical device or a sheath through which a medical instrument can be deployed, and wherein the tissue access site is defined by at least one tissue flap having a predetermined geometry; and
a tissue closure device comprising at least one tube positioned about an axis of the tissue closure device, wherein the at least one tube contains at least one suture therein, wherein the at least one tube is configured for attaching the at least one suture to the tissue wall at a location corresponding to the at least one tissue flap, and wherein the at least one blade extends radially outward beyond the at least one tube.

18. The tissue access site system of claim 17, wherein the tissue cutting element and the tissue closure device are coaxial with one another, wherein the tissue cutting element and the tissue closure device are configured to translate axially with respect to one another, and wherein the tissue cutting element and the tissue closure device are rotationally keyed to one another.

19. The tissue access site system of claim 17, further comprising a housing configured for guiding the tissue cutting element and the tissue closure device toward the tissue wall, wherein the tissue cutting element is configured for moving from a storage position in which the at least one blade and the central rod are positioned within the housing to a deployed position in which the at least one blade and the central rod extend out of the housing, and wherein the tissue closure device is configured for moving from a storage position in which the tubes are at least one tube is positioned within the housing to a deployed position in which extend at least one tube extends out of the housing.

20. A tissue access site system comprising:
a tissue cutting element comprising a central rod and a plurality of blades extending from the central rod, wherein the blades and the central rod are configured to be jointly penetrated through a tissue wall to generate a tissue access site configured to accommodate insertion of a medical instrument or a sheath through which a medical instrument can be deployed, and wherein the tissue access site is defined by a plurality of tissue flaps having a predetermined geometry; and
a tissue closure device comprising a plurality of tubes positioned in a circumferential array about an axis of the tissue closure device, wherein each tube contains a suture therein, wherein the tubes are configured for attaching the sutures to the tissue wall at locations corresponding to each of the tissue flaps, and wherein each blade extends radially outward beyond adjacent tubes.

21. The tissue access site system of claim 20, wherein each blade is positioned circumferentially between adjacent tubes.

22. The tissue access site system of claim 20, wherein the tissue cutting element and the tissue closure device are coaxial with one another, wherein the tissue cutting element and the tissue closure device are configured to translate axially with respect to one another, and wherein the tissue cutting element and the tissue closure device are rotationally keyed to one another.

23. The tissue access site system of claim 20, further comprising a housing configured for guiding the tissue cutting element and the tissue closure device toward the tissue wall, wherein the tissue cutting element and the tissue closure device are configured for being separately deployed from the housing.

24. The tissue access site system of claim 23, wherein the tissue cutting element is configured for moving from a storage position in which the central rod and the blades are positioned within the housing to a deployed position in which the central rod and the blades extend out of the housing, and wherein the tissue closure device is configured for moving from a storage position in which the tubes are positioned within the housing to a deployed position in which the tubes extend out of the housing.

25. The tissue access site system of claim 23, wherein the housing comprises a plurality of cutting element tracts configured for guiding the blades toward the tissue wall, and a plurality of channels configured for guiding the tubes toward the tissue wall.

* * * * *